United States Patent
Nempont et al.

(10) Patent No.: US 9,600,885 B2
(45) Date of Patent: Mar. 21, 2017

(54) TEMPORAL ANATOMICAL TARGET TAGGING IN ANGIOGRAMS

(71) Applicant: KONINKLIJKE PHILIPS N.V., Eindhoven (NL)

(72) Inventors: Olivier Pierre Nempont, Suresnes (FR); Pascal Yves Francois Cathier, Asnières-sur-Seine (FR); Raoul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/408,399

(22) PCT Filed: Jun. 10, 2013

(86) PCT No.: PCT/IB2013/054733
§ 371 (c)(1),
(2) Date: Dec. 16, 2014

(87) PCT Pub. No.: WO2013/190422
PCT Pub. Date: Dec. 27, 2013

(65) Prior Publication Data
US 2015/0206308 A1   Jul. 23, 2015

(30) Foreign Application Priority Data
Jun. 22, 2012 (EP) .................................... 12305721

(51) Int. Cl.
*G06T 7/00* (2006.01)
*A61B 6/00* (2006.01)
*G06F 19/00* (2011.01)

(52) U.S. Cl.
CPC ............ *G06T 7/0038* (2013.01); *A61B 6/461* (2013.01); *A61B 6/463* (2013.01); *A61B 6/469* (2013.01);
(Continued)

(58) Field of Classification Search
USPC ......................................................... 382/131
See application file for complete search history.

(56) References Cited

U.S. PATENT DOCUMENTS 5,389,101 A * 2/1995 Heilbrun .................. A61B 5/06
348/E13.014
6,004,270 A * 12/1999 Urbano ............... G01S 7/52034
600/440
(Continued)

FOREIGN PATENT DOCUMENTS

WO     20100063389 A1    6/2010

OTHER PUBLICATIONS

Preim et al, "Survey of the Visual Exploration and Analysis of Perfusion Data", IEEE Transactions on Visualization and Computer Graphics, vol. 15, No. 2, Mar. 1, 2009, pp. 205-220.
(Continued)

*Primary Examiner* — Jason Heidemann
*Assistant Examiner* — Brian Shin (57) ABSTRACT

An image processing apparatus and method take as input a pre-op reference image (OP) and a stream (A) of angiographic images (A1-A3). Based on multiple pre-defined regions of interest (ROIa-c) in the pre-op reference image (PO), the angiographic image best showing when displayed a respective one of the regions of interest (ROIa-c) is detected from among the stream (A) of angiographic images (A1-A3). The detected angiographic image is associated with the region of interest to form an associative data structure (DS). A graphical user interface (GUI) is generated that allows based on the associative data structure (DS) to retrieve the associated angiography upon a user selecting any one of the regions of interest (ROIa-c) on the graphical user interface (GUI).

12 Claims, 4 Drawing Sheets

(52) U.S. Cl.
CPC .............. *A61B 6/481* (2013.01); *A61B 6/486* (2013.01); *A61B 6/488* (2013.01); *A61B 6/504* (2013.01); *A61B 6/507* (2013.01); *A61B 6/5217* (2013.01); *A61B 6/5247* (2013.01); *A61B 90/37* (2016.02); *G06F 19/321* (2013.01); *G06F 19/3406* (2013.01); *A61B 2090/374* (2016.02); *A61B 2090/3762* (2016.02); *G06T 2200/24* (2013.01); *G06T 2207/10116* (2013.01)

(56) References Cited

U.S. PATENT DOCUMENTS

| | | | |
|---|---|---|---|
| 6,614,453 B1* | 9/2003 | Suri | G06F 19/321 345/419 |
| 6,645,147 B1* | 11/2003 | Jackson | A61B 8/06 600/458 |
| 7,346,202 B1 | 3/2008 | Schneider | |
| 7,650,179 B2 | 1/2010 | Redel et al. | |
| 7,761,136 B2 | 7/2010 | Ohishi et al. | |
| 2010/0063389 A1 | 3/2010 | Florent | |
| 2010/0249582 A1 | 9/2010 | Feuerlein et al. | |
| 2011/0123079 A1* | 5/2011 | Gustafson | G06F 19/321 382/131 |
| 2011/0255763 A1* | 10/2011 | Bogoni | G06T 19/00 382/131 |

OTHER PUBLICATIONS

Oeltze et al, "Interactive Visual Analysis of Perfusion Data", IEEE Transactions on Visualization and Computer Graphics, vol. 13, No. 6, Nov. 1, 2007, pp. 1392-1399.

Kirbas et al, "A Review of Vessel Extraction Techniques and Algorithms", ACM Compuoting Surveys, vol. 30, 2004, pp. 81-121.

Lesage et al, "A Review of 3D Vessel Lumen Segmentation Techniques: Models, Features, and Extraction Schemes", Medical Image Analysis, vol. 13, 2009, pp. 8199-8845.

Mory et al, "Non-Euclidean Image-Adaptive Radial Basis Functions for 3D Interactive Segmentation", IEEE 12 International Conference on Computer Vision, 2009, pp. 787-794.

Markelj et al, "A Review of 3D/2D Registration Methods for Image-Guided Interventions", Medical Image Analysis, vol. 16, 2012, pp. 642-661.

Carrell et al, "Feasibility and Limitations of an Automated 2D-3D Rigid Image Registration System for Complex Endovascular Aortic Procedures", Journal of Endovascular Therapy, vol. 17, 2010, pp. 527-533.

You et al, "Spatio-Temporal Analysis for Automatic Contrast Injection Detection on Angiography During Transm-Catheter Aortic Valve Implantation", IEEE International Symposium, 2011, pp. 702-706.

Olabarriaga et al, "Segmentation of Thrombus in Abdominal Aortic Aneurysms From CTA With Non-Parametric Statistical Grey Level Appearance Modelling", IEEE Transactions on Medical Imaging, vol. 24, 2005, pp. 477-485.

\* cited by examiner

TEMPORAL ANATOMICAL TARGET TAGGING IN ANGIOGRAMS

CROSS-REFERENCE TO PRIOR APPLICATIONS

This application is the U.S. National Phase application under 35 U.S.C. §371 of International Application Serial No. PCT/IB2013/054733, filed on Jun. 10, 2013, which claims the benefit of European Serial No. EP12305721.8, filed on Jun. 22, 2012. These applications are hereby incorporated by reference herein.

FIELD OF THE INVENTION

The present invention relates to an image processing apparatus, to a method of image processing, to an image processing system, to a computer program element and to a computer readable medium.

BACKGROUND OF THE INVENTION

During endovascular interventions catheters are inserted into a patient's vascular system to reach a target or treatment area for instance to deploy a stent. This is generally done under fluoroscopic control. As the vasculature is poorly visible, contrast agent may be injected using specific catheters. During an angiography, the contrast agent propagates through the vascular system with the blood flow. The frame where the target anatomy is the most visible is generally selected and displayed afterwards next to a live image.

However, in some interventions such as Endovascular Aneurysm Repair (EVAR), the region where the contrast agent is administered to the object of examination is relatively far from a target region.

What is more, during a single intervention session there may be several anatomical regions of interest that are spread far apart and need be screened during a single angiographic session. For instance, EVAR interventions cover a wide area ranging from the renal arteries to the femoral arteries. In these situations, a selection of several frames would be required to cover all the target regions.

A method for selecting frames of angiograms using a "live" tip position of a catheter is described in applicant's WO2010/0063389.

SUMMARY OF THE INVENTION

There may therefore be a need for an apparatus to help navigate angiograms. The object of the present invention is solved by the subject matter of the independent claims wherein further embodiments are incorporated in the dependent claims.

It should be noted that the following described aspects of the invention equally apply to the method of image processing, to the image processing system, to the computer program element and to the computer readable medium.

According to one aspect of the present invention there is provided an image processing apparatus comprising:

input unit receiving a stream of frames, the stream of frames acquired whilst a volume of contrast agent is propagating through an object of interest, the contrast agent volume passing a plurality of regions of interests (ROIs) and perfusing respective ones of the plurality of ROIs as the contrast agent volume propagates through the object;

a registration unit configured to register a plurality of said frames onto a pre-op reference image data set, the reference image set including segmentations of the ROIs;

an identifier configured to identify for each of the plurality of said ROIs a main frame acquired at a time when a concentration of the contrast agent volume at the respective ROI is higher than a pre-defined threshold an associator configured to associate each of the plurality of ROIs with a respective one of the identified main frames thereby forming an associative ROI-frame data structure; and an output unit configured to generate a user-interface (UI) based on said associated data structure, the UI when displayed on a screen allowing a user to select any one of the ROIs, the output unit in response to said selection controlling the screen to display the main frame associated with said selected ROI, the user interface thereby affording to the user temporal navigation through the stream of frames.

According to one embodiment the stream or sequence of frames are angiograms ("angios") acquired by an X-ray imager and include at least one projection view of at least one of the ROIs. In one embodiment the ROIs are parts of a patient's anatomy that are considered relevant for an intervention during which the angios are acquired.

In one embodiment, it is the frame with the highest or maximum contrast agent concentration at the respective ROI that is identified, flagged up as the main frame and then forwarded to associator. The contrast agent concentration threshold is directly related to the image contrast at the respective image portion that corresponds to a footprint of the perfused ROI in the respective frame. Said ROI footprint stands out at a higher contrast (in terms of pixel values) as compared to the image portion outside the footprint's boundary of the frame's image plane so appears normally "darker" or brighter than the image portion depending on the pixel value-to-grayscale encoding or mapping chosen for the frames when displaying same on the screen. The identifier therefore uses in one embodiment pixel value thresholding to identify the frame that was acquired when there was sufficient contrast agent concentration at the respective region of interest. According to one embodiment the threshold is chosen so that the "main" frame is identified, that is, the frame acquired when the contrast agent concentration at the respective ROI was at substantially at its maximum so the region is shown darkest or with best contrast compared to other frames in the stream. The contrast threshold for an image portion may be defined in term of an average pixel grey value gradient across said portions boundary or the average of the pixel grey values enclosed by the boundary of said region or evolution of the mean value over time.

The segmented or delineated ROIs are user pre-defined image portions in the reference image. So the reference image via its segmented ROIs "guides" the associator in its operation to build up the data structure. The user effects the segmentations either manually or via a semi-automatic segmentor in the reference image before the stream of angios are received. In one embodiment, the regions of interest are produced by a suitably programmed automated segmenter. In one embodiment, the reference image data set that includes the 3D or 2D segmentations is a 3D CT or MR image volume that has been taken of the object so as to include views of the ROIs. However in other embodiments the reference image may also be a 2D image. The reference image is a pre-op image, in other words, it is acquired from the object before the stream of angios is acquired.

The data structure produced by the image processor IP may be looked at as a family of "local" timelines, one for each of the ROIs. Each timeline shows by way of the associated frames the perfusion with contrast agent of the respective ROIs during the angiography. In one embodiment, there is also a global timeline produced from said family of timelines where a set of perfused anatomic structures including the ROIs is associated to each frame and a perfusion evolution curve can be computed from same and associated to the respective anatomic structure.

According to one embodiment, the global timeline is a mapping between frame indices and labels that correspond to the ROIs in the pre-op image data set. The ROIs may be annotated with their respective anatomic name. Each frame index is associated to a set of labels. Each label refers to those ROIs that are perfused or filled with contrast agent at a level as specified by the contrast threshold in terms of pixel brightness. In the local timeline, each label is associated to a frame where the ROI referred to by said label is the most visible or is associated to a set of frames indices where the contrast (or concentration of contrast agent at acquisition time of said frames) is at least as specified.

According to one embodiment the apparatus is configured to extend said data structure by including into same "intermediate anatomic structures" whose segmentations are also in the pre-op reference in addition to the segmentations of the ROIs.

The apparatus affords to the user a "semantic" temporal navigation within the received stream of angiograms because relevant frames can be retrieved upon the user specifying the anatomic name, that is the label, of the ROI they wish to see in the angio frame where it is "best" filled (perfused) with contrast agent. The apparatus may help the interventionist to easily navigate within the stream of frames during the procedure by automatically selecting the background appropriate frames and making them available upon user request. The produced data structures, that is the global timeline or the family of local timelines may also be used as input of subsequent processing steps.

No real "live" presence of in-situ medical devices such as catheter tips are required. Instead, the apparatus as proposed herein uses solely in-image information from the reference image and the received angios to obtain the data structure. The formed data structure facilitates retrieval of an angiogram that show a desired one the ROIs in sufficient contrast or that show.

According to one embodiment, the identifier is configured to further identify frames acquired before or after said respective main frame, the associator configured to likewise associate said further frames with the respective ones of said ROIs, the data structure thereby recording for each ROI a timeline of the contrast agent perfusion. In other words, the respective further frames record the passage of the volume of contrast agent through the respective regions of interest. In this embodiment the threshold is so chosen so as to identify also the frames where the concentration of contrast agent in the respective ROIs is still sufficiently high but not as high as for the main frame. Including said further frames into the data structure facilitates retrieval of angios that show the local evolution of contrast agent concentration at a user-select one or ones of the ROIs.

According to one embodiment, the associator is configured to associate for each of the ROIs a localized curve showing the evolution of contrast agent concentration at the respective ROI, the curve based on image information in the respective sequence of main frames and further frames.

According to one embodiment, the apparatus updates the data structure as the contrast agent is propagating through the object and as more angios are received.

According to one embodiment, the generated UI is a graphical UI (GUI) that includes interactive buttons each associated with a respective one of the ROIs. Each button bears an annotation indicative of the anatomic name or function of the respective ROI.

According to one embodiment, the UI allows the user to toggle through the main and further frames associated with a respective one from among the ROIs or through the main frames and the further frames associated with any one of a user-definable selection from among the ROIs.

According to one embodiment, the timelines may be represented by rendering on the GUI each label as a color bar. The color bar extends in a displayed table of frame indices along indices of those frames where the anatomical structure referenced by the respective label is displayable at sufficient contrast due to the amount of contrast agent present at acquisition time of said respective frame.

This invention may be used in an X-Ray Cathlab system.

It is understood that is some embodiments, the image processor may only operate on one ROI from among the plurality of ROIs or on a user-defined sub-selection from among the plurality of ROIs rather than on each of the ROIs in the plurality of ROIs. In some embodiments the pre-op reference may include only a single ROI with one segmentation for said single ROI. In those embodiments it is only for the one ROI or for each of the sub-selected ROIs that the main frame and further frames are identified by identifier and then respectively associated by associator. The data structure may therefore include in an extreme case only one association or fewer associations than the number of ROIs in the plurality of segmented ROIs in the reference image.

DEFINITIONS

Angiograms ("angio") are 2D projection images taken after a contrast agent is resident in the object's vasculature thereby conferring opacity to same during X-ray image acquisition. In Fluoroscopy 2D projection images, no contrast agent is resident so it is general only the medical device such as catheter (along with other radiation opaque matter such as bones, thick muscle tissue etc.) that is visible when the fluoroscopy image is displayed whereas the vasculature soft tissue is not discernible when the fluoroscopy image is displayed.

"View" and "projection direction" is used interchangeably herein.

"Tag" may denote the name or label of a ROI in the pre-op reference image or data.

"Segmentation" or "delineation" is used interchangeably herein and is effected by an operator or by an algorithm on the ROIs as represented in the reference image. It is those delineations or segmentations that are then feed into the image processor.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
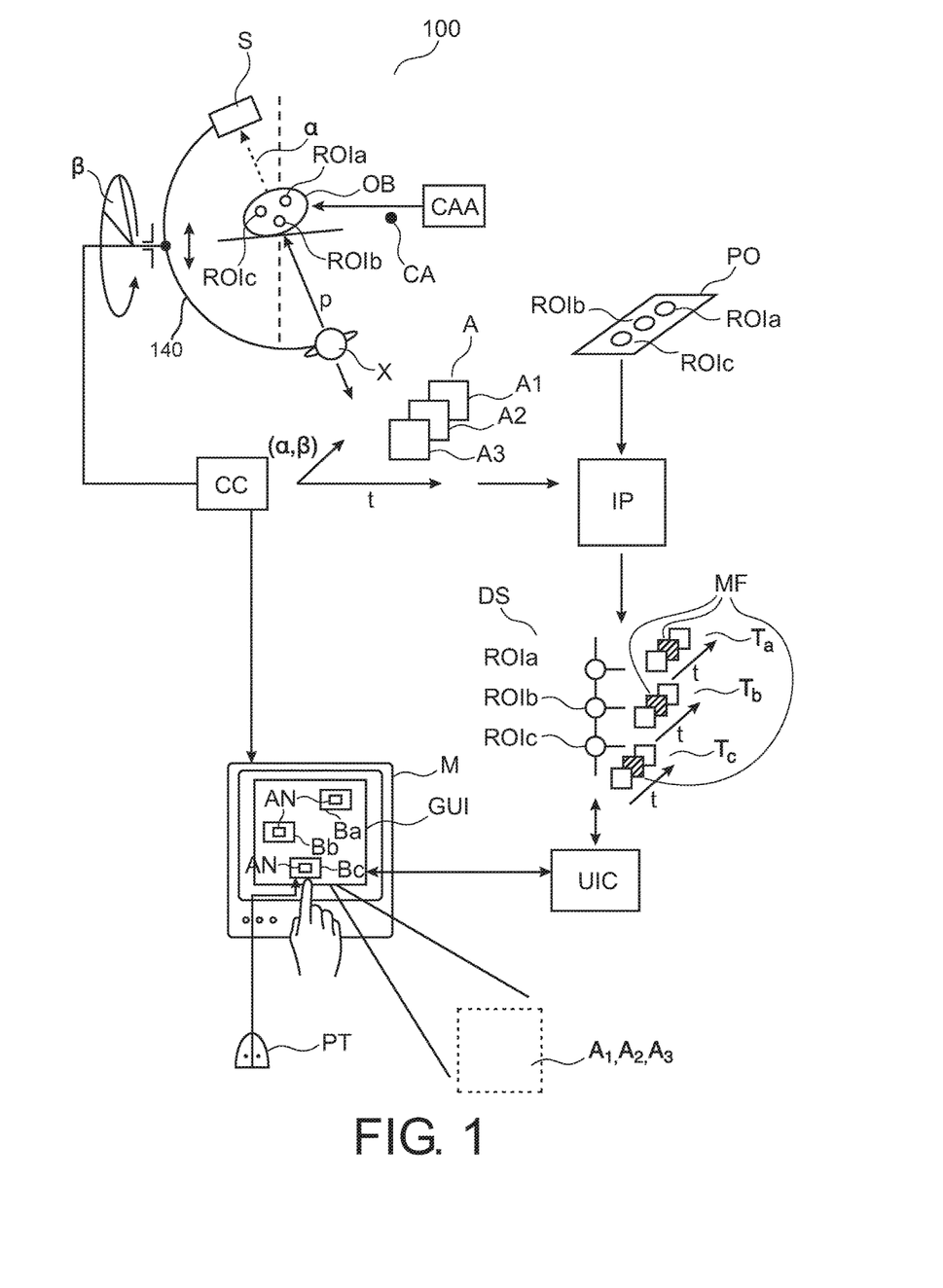
FIG. 1 shows a block diagram of an image processing system.

FIG. 1 shows an image processing system including an x-ray imager 100 of the C-arm type. X-ray imager 100 is used in an intervention to capture a stream or sequence of x-ray projection images A1-A3 of an object OB (for example a patient). In one embodiment, the organ of interest is a patient's pelvis region in an EVAR intervention.

The object OB or patient is placed on an examination table during the intervention. Imager 100 comprises a rigid C-arm 140 journaled on a bearing. Journaling allows rotation of C-arm 140 around a first axis passing through journaling. C-arm 140 can thus be positioned at various rotation angles α around object OB. C-arm 140 is further rotatable around an axis perpendicular to the first axis to so assume different angulation angles β so that C-arm 140 enjoys at least 2 degrees of freedom. However those of skill in the art will appreciate that the above characterization of the C-arm degrees of freedom in terms of angle alpha/beta is for illustrative purposes and that a full characterization of the C-arm imaging geometry has in fact more than 2 degrees of freedom.

C-arm 140 carries at one of its ends an x-ray source X and at the other end a detector S in opposed spatial relationship to x-ray source X. The detector S includes an array of detector cells (not shown).

X-rays are emitted from x-ray source X. The X-rays pass through object OB and are then detected at detector X. The X-rays are formed from X-ray beams p.

Each x-ray beam p is attenuated as it passes through the object OB's vasculature and impact on same. It is this attenuated x-ray beam that is detected at detector S.

The angle of incidence ("projection direction") at which the x-ray beam impacts vasculature is defined by the pair (α, β) of rotation angle α and angulation angle β. The degree of attenuation experienced by each individual x-ray beam p depends on the type and amount of tissue the ray p is passing through. Each attenuated x-ray beam p impinges on a detector cell and generates there an electric signal anti-proportional to the degree of attenuation. The electric signal generated at each detector cell for an impinging x-ray beam p is then translated via a data acquisition system (not shown) into a pixel value encoding a corresponding grey value. The pixel values are then stored in a matrix structure forming a projection image taken at a particular projection direction (α, β). The angles (α, β) form the imaging geometry possibly including further parameters to specify the spatial relationship between beam and patient. It is understood that in imagers other than c-arm imagers different angles or other quantities specify the projection direction relative to the patient.

The stream of projection images A is acquired during the image acquisition epoch or intervention of the object OB with individual projection images A1, A2, A3 acquired generally along different projection directions and a number of angios acquired throughout a given period for the same imaging geometry. The sequence A of projection images may then be stored on a data base (not shown) for later retrieval. The projection images A1-A3 may be stored in DICOM format. The DICOM format includes meta-data encoding for each projection image the projection direction at which it was acquired along with its acquisition time t.

Vasculature in itself has no or significantly less radiation opacity than the surrounding tissue meaning that the projection ("footprint") of vasculature would not normally be visible in the projection images A1-A3. To remedy this, a volume of contrast agent CA is administered via suitable contrast agent administrator CAA such as a power injector to patient OB shortly prior to the image acquisition by C-arm imager 100. Contrast agent gradually propagates through object OB's vasculature and so confers radiation opacity to same. Because of the contrast agent, in each projection image A1-A3 (also known as angiograms or "angios") includes a projection view along a projection direction or a footprint of the part of the vasculature or organ that is perfused at the time the respective image is A1, A2 or A3 is taken.

The stream A or sequence of angios A1-A3 acquired during the invention form a high dimensional image data block that gradually grows as the intervention progresses and more and more angios A1-A3 are acquired.

The intervention may last for about five minutes with individual frames A1-A3 acquired at a rate of about 3 frames per second for abdominal interventions and up to 15 frames per second for cardiac interventions. The total number of frames A in the stream can therefore easily run into many hundred frames even more than a thousand images A1-A3. The block is multi-dimensional because each frame A1-A3 includes two dimensional image information in form of pixel grey values at each position x,y and each image is indexed by its imaging geometry and its acquisition time. Generally, at a given time during the intervention a plurality of frames are acquired at a fixed imaging geometry position.

The operation of imager C-arm imager 100 is controlled by a human operator from a central computer console CC. Computer console CC includes suitable actuation means such as a joy stick for example which allows the operator to adjust the imaging geometry during the intervention. Computer console CC also allows (for example via said joystick controller) the operator to trigger the exposures to acquire the individual frames A1-A3. Computer console CC is in communication with a monitor M. Console CC may also run suitable viewer software that allows viewing the individual angios A1-A3 on screen M.

Object OB includes in general a number of different regions of interests ROIa-ROIc which are to be examined during the intervention. Examples are the introduction of a catheter which is to visit any one of those regions of interest ROIa-c.

Figure 2:
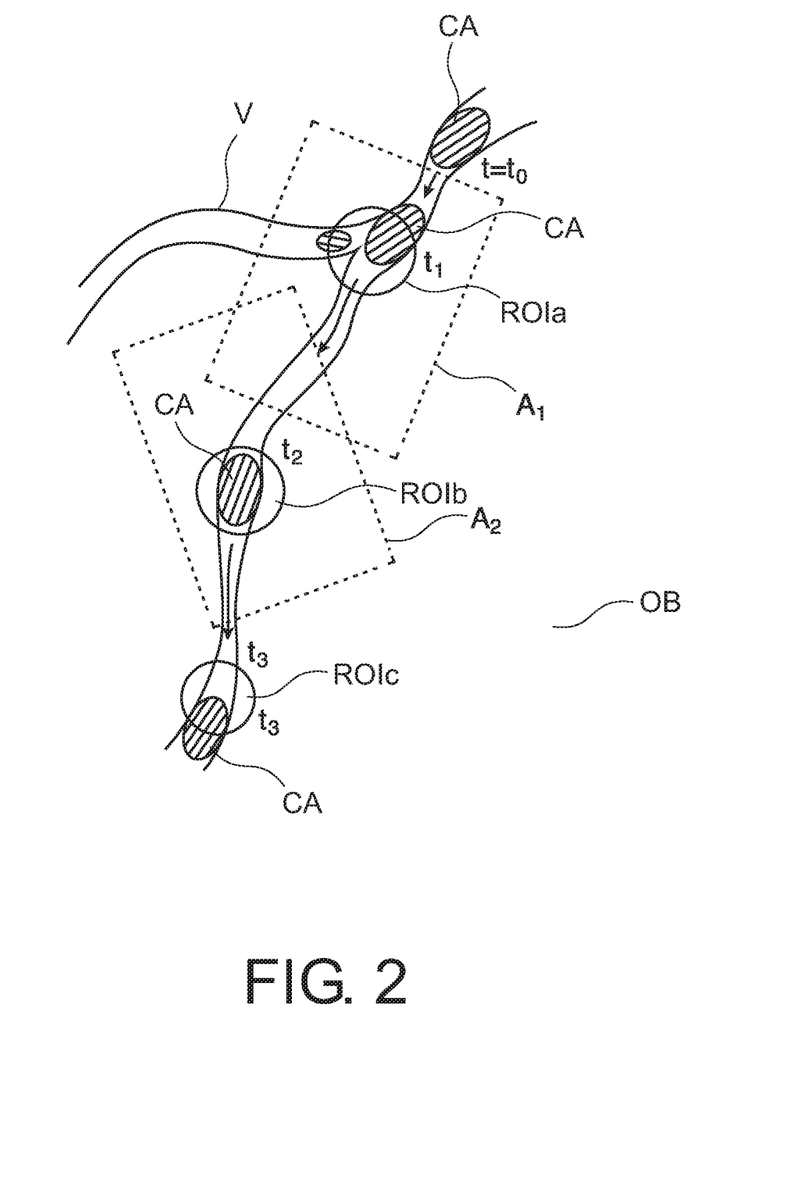
FIG. 2 shows a schematic view of an anatomic area with contrast agent.

With reference to FIG. 2, a schematic view on a relatively large part of the anatomy of object OB is shown. The previously administered volume CA of contrast agent ("bolus") travels or propagates with the flowing blood through vessel V and passes the individual regions of interest ROI a-c one by one as time progresses thereby perfusing in turn any one of region of interests ROIa-c.

Although bolus is shown in FIG. 2 as having a defined (oval) shape, it is understood that in reality said bolus will diffuse throughout the vessel with the volume smearing out as time progresses. For a sufficiently short period of time however and as depicted in FIG. 2 the bolus can be thought of as moving point or center region around which the bulk of the contrast agent volume is concentrated.

It can be seen that the amount of profusion by the volume of contrast agent CA of each individual region of interest (ROI a-c) changes with time. In other words the contrast agent concentration curve over time at each of the positions ROI a-c is roughly a bell shaped curve with its respective peak when the concentration of contrast agent at the respective location ROI a-c is at its maximum.

In some interventional situations and as schematically shown in FIG. 2, no single angio A1-A3 is capable of showing all the regions of interest ROI a-c which are spread across a relatively large anatomical region. What is more, because of the bolus' dynamics, the instants $t=t_1$, $t_2$ or $t_3$ at which any single ROIa-c is perfused at maximum with contrast agent is in general different, so the angios A1-3 where any one of the ROIa-c is shown at highest contrast are different.

Now, referring back to FIG. 1 the image processing system further comprises an image processor IP that supports the intervention task by automatically finding and selecting from the stream A of angios those "main" frames MF among angios A1-A3 where at least one of the regions of interest ROI a-c are shown as filled with appropriate amount of contrast agent to so allow viewing same with maximum contrast or at least at a contrast higher than an adjustable threshold value definable in terms of in-image pixel value brightness. The main frames were acquired at a time when the contrast agent concentration was at its maximum in at least one of the regions of interest ROI a-c. In other words, the main frame MF is that frame where the respective ROIa-c is most visible when viewed or was acquired when "best filled" at the respective ROI with contrast agent CA.

Image processor IP takes as input the stream of angiograms A as they are required during the intervention and a reference image PO. Reference image PO of object OB may be a previously acquired MR or CT 3D data volume set. The particular imaging geometry used for acquisition of said reference PO is thought to be either encoded in the block itself for example as DICOM metadata or it can be retrieved from a suitable data base where that information is held.

Reference image PO is previously "tagged" or segmented either automatically or manually by the operator into a number of distinct anatomic structures, that is individually addressable image portions with a defined boundary each representative of an anatomic structure that is either a ROI or an intermediate structure. Segmented anatomical structures include the regions of interest ROIa-c but also possibly further anatomic structures. In one embodiment, each segmentation is annotated that is indexed by a tag that can be translated upon look-up in an anatomical database into a string of natural language description (for example, the anatomic name of the anatomic structure) whose projective footprint is represented by the respective segmentation.

Broadly speaking the apparatus image processor IP produces as an output a data structure DS that may be referred to as the "ROI-frame" associative data structure. In data structure DS, each region of interest ROIa-c is associated with a selection of angios that were acquired at a time when the bolus was passing through that region of interest ROIa, ROI b or ROIc. The selection of angios so associated with region of interest ROIa, ROI b or ROIc include the respective main frame for that region of interest ROIa, ROI b or ROIc. So each region of interest ROIa-c is associated with a "local" timeline Ta-Tc showing the evolution of contrast agent CA concentration at the respective location or region ROIa-c.

According to one embodiment, data structure DS may be extended. In the extended data structure, each incoming angio A1-A3 is associated with the respective anatomic structure that is most visible in the respective angio A1-A3 but which may not be among the pre-defined regions of interest ROIa-c as per reference image OP. In other words, the so extended data structure forms a "global" timeline of consecutively perfused anatomical structures whilst the bolus was travelling through vessel V as the angios are acquired during its passage. Anatomic structures visited by the bolus as its travels between the predefined regions of interest can thus be included. In one embodiment the data structure may be re-mapped or converted into a "frame-ROI" data structure so that it is now each frame that is associated with the respective ROI or intermediate anatomic structure that is shown in the respective frame with sufficient contrast as previously determined by identifier ID.

Accounting also for said "non-ROI" intermediate anatomic structures adds flexibility should those structures unexpectedly become relevant during the intervention. This also allows accounting for segmentations in the pre-op image that were initially not intended but were still produced when for example an fully-automatic segmenter was used to segment the pre-op reference image.

The data structure whether extended or not can then be used by a user interface controller UIC to back-end support an interactive graphical user interface GUI for display on screen M with which the operator can conveniently interact to navigate through the stream of acquired angios. The GUI affords easy and intuitive retrieval of an angio from the received stream A of angios most relevant for an intervention instant. The relevant angio may be the one that best shows a particular region of interest ROIa-c or a user-selectable set of those ROIs. The user may also select a desired "intermediate" anatomic structure which the bolus visited on its passage though the imaged vessel between the regions of interest ROIa-c.

According to one embodiment it is the anatomic identifiers as obtained from segmented reference image PO that are associated in the data structures with the respective frame. The reference image PO can be thought of as a dictionary of the anatomic structures in the object OB which are then assigned to the respective angios.

It is understood that each individual angio may show more than one intermediate structures or regions of interest ROIa-c so may get assigned to it more than just one identifier.

According to one embodiment image processor operates in real-time or "online", so the data structure DS is built up gradually as the stream of angios are acquired during the intervention and as they are received at the image processor IP.

In another alternative "offline" embodiment however, first, all angios for the particular intervention are acquired and it is this complete stream that is then fed into image processor (IP). It is only the complete data structure that is output and made available or is forwarded to UIC. The previous online embodiment is preferred because it allows for a quicker processing "on-the-fly" and a subsequent "piping" or feeding (in real-time) into further image post processors.

Broadly speaking, image processor outputs data structure DS as a collection or family of annotated timelines Ta-c of angios, each timeline representing how the respective ROI is perfused during the intervention or outputs a global timeline of perfused structures with each respective angio associated to respective ROIs or intermediate anatomic structures. The collection of timelines may be used as a navigation tool in the GUI. The timelines or the frames referenced by same may also be forwarded as input to other image processors such as an automatic delineation algorithm to compute the boundary of the ROIs as per the angiograms. The so computed boundaries can then be used as overlay graphics on a "live" fluoroscopy image which is displayed on a separate monitor during the interventions and which shows the silhouette of the catheter or guide-wire used in the intervention. The automatic delineation step may be needed to account for differences in the boundaries of the projected ROI segmentations and the actual boundary as shown in the respective angiogram.

Operation

Figure 3:
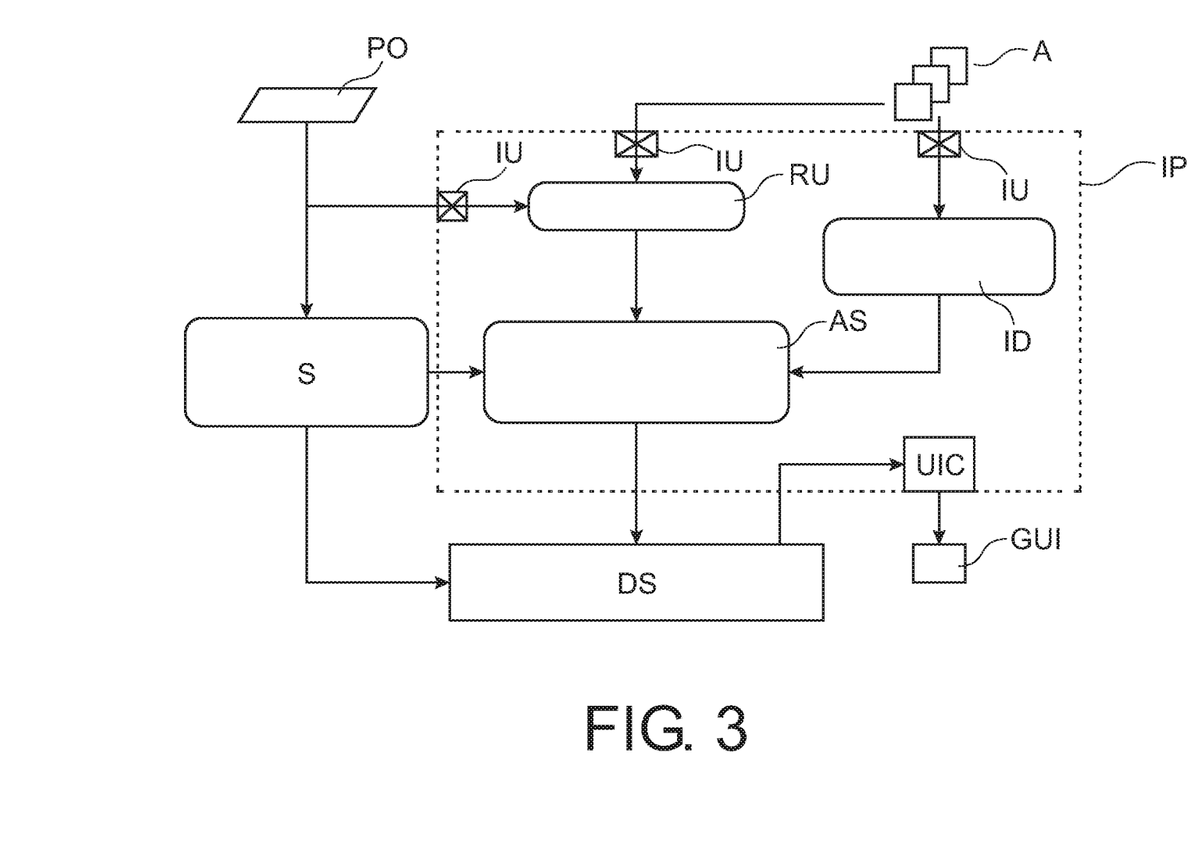
FIG. 3 shows a block diagram of an image processor in the system of FIG. 1.

With reference to FIG. 3 the operation of image processor IP will now be explained in more detail.

Image processor IP receives via suitable input interfaces IU i) reference image PO having annotated and segmented anatomical structures and ii) the stream of angios A. The anatomical region in the reference pre-operational image PO corresponds to the region of the object OB that is to be screened during the intervention. The different anatomical structures including the intended regions of interest ROI a-c are assumed to be detectable so a previous use of contrast agent when recording said reference image may have been required.

The angios A are assumed to encode in their meta-data the respective acquisition or imaging geometry used when acquiring each angio A1-A3. Said angio imaging geometry may also be retrieved separately by image processor IP form an external data base (not shown). Segmentation of the pre-op reference PO was executed by a segmentor S. The segmentation or tagging of anatomical structures in the pre-operational reference image PO can be achieved by generic algorithms either automatically or semi-automatically to extract discernible anatomic structures in the 3D volume. The position of the pre-operational reference image PO relative to the x-ray imager 100's frame of reference is then established by registrator unit RU. In other words the 3D data volume and each of the angios are aligned along a common reference coordinate system. The common coordinate system enables finding corresponding "footprints" of the same delineated anatomical structure throughout both the 3D data volume PO and each of the angios. Registration is performed on each frame of the angios A but may also be performed on only select ones of the Angios. In an embodiment, low quality angios or angios that can be a priori excluded to contain no useful or relevant data may be excluded from registration thereby saving CPU time.

According to one embodiment, registration unit RU establishes the position of the 3D volume relative to the angios by using one or several projections on top of the current angiogram. For this purpose in some embodiments there are additional fluoroscopy images that are used that are acquired at different C-arm positions of C-arm imager 100. Registration unit RU outputs for each angio a rigid or no-rigid affine registration transformation with which the alignment of the respective angio and the reference image PO along the common coordinate system can be effected.

Identifier ID screens each or a selection of angios to establish which part of the anatomy was perfused when the respective image was acquired. According to one embodiment a contrast agent map is computed for each of the angios. In one embodiment a pixel-wise difference image is established in respect to a base line image where no contrast is show, if it can be assumed there was no movement of the patient during acquisition of those frames. If however there was patient movement, more advanced subtraction techniques can be used to compensate said motion. Identifier ID outputs for each angio in terms of image pixel coordinates an image portion that outlines the contrast agent perfused part in the respective image. Grey value thresholding may be used to establish said perfused angio portions.

The collection of registration transformations as provided by registration unit RU and the identified perfused portion in the angios as provided by identifier ID are then forwarded to associator AS. For each angio, the respective registration transformation is then applied in turn to segmented region of interest ROIa-c in the reference image PO which is thereby projected into the aligned image plane of the respective angio under consideration. The so obtained projected footprint of the respective ROIa-c is then attempted to be matched up by the associator AS to the image portion in the respective angio as identified by identifier ID. If a match is registered, the angio is flagged up accordingly and is then associated with the respective region of interest ROIa-c. In this manner data structure DS is gradually built up as the associator iterates through each angio for each segmentation of the regions of interest ROIa-c as recorded in reference image PO. The data structure DS may be based on the associative array data type known for example in Perl as a "hash" or as a "maps" in C++. In one embodiment, once a match is registered, this fact is immediately indicated to the operator by a visual clue, for example, a flashing widget on the graphical user interface GUI or by an acoustic signal issued by the computer console CC. For the matching, a grey value thresholding can be used to adjust the matcher's responsiveness. In this manner it is not only the main frame that is matched up and associated with the respective region of interest ROIa-c but also angios that were acquired around an interval before and after the main frame's acquisition time. The length of said interval is a function of the grey value threshold. Each main frame MF, once included by associator in the data structure is flagged up accordingly to facilitate its later retrieval. Neighboring frames acquired before and after main frame can be indexed by their acquisition time relative to the main frame's acquisition time.

As mentioned earlier, according to one embodiment associator AS is configured to extend data structure DS to also associate intermediate anatomic structures with respective one of the frames. Intermediate anatomic structures are those that are not among the pre-defined ROI segmentations in the pre-op reference image PO. To this end associator AS is configured to operate a converse matching if no match for a given angio with any of the pre-defined regions of interest ROIa-c is registered. In converse matching, the identified perfused portion in said "no match" angio is projected into the reference image PO and a match with an anatomic structure other than the regions of interests ROIa-c is attempted. If a match is found, said anatomic intermediate anatomic structure is then associated with that non-region-of interest angio. In this manner each angio can be associated with the anatomical structure that was perfused when said angio was acquired. In this manner the anatomy-frame-extended data structure DS can be built-up as the associator iterates through the stream A of received angios. Data structure DS whether extended or not is then made available to user interface controller UIC which then can use this information to provide the operational back-end for graphical user interface GUI.

Referring again to FIG. 1, the functionality afforded by said graphical user interface GUI is now explained in more detail.

In one embodiment a slice from reference image PO is shown on GUI as a background image overlaid with interactive button Ba, Bb, Bc each referring to respective ones of the ROIa-c or may include further button for other intermediary structures as desired. Actuation of either of the buttons Ba-c by a pointer tool PT such as computer mouse or by touch if monitor M is a touch screen, calls on UIC to retrieve the respectively associated angio recorded in data structure DS. Repeated actuation of button Ba-c would allow toggling through the main frame and the respective further frames associated with the respective region of interest ROIa, ROIb or ROIc. In one embodiment there is also the option to select for example by consecutive mouse-right-click action more than one button, say Ba and Bb. Actuation of any one of the selected buttons Ba, Bb would than allow cycling or toggling through all of the main frames and further frames associated with regions of interest ROIa, ROIb referred to by button Ba or button Bb. In the online embodiment, the respective buttons Ba-c would "pop-up" as the image processor processes the incoming stream of angios and once the respective main frame has been found. In one embodiment a notifier signal is issued such a flashing icon or other GUI widget or an acoustic signal, so as to notify for each region of interest ROIa-c that the respective main frame has been found and that the apparatus is now ready to retrieve same.

According to one embodiment, Buttons Ba-c include annotations AN for the respective anatomic structures.

In one embodiment, the buttons are formed as outlined image portions of the respective region of interest as shown in the currently displayed slice of reference image PO.

In one embodiment the retrieval button Ba-c are arranged as interactive elements of a table each bearing one of the annotations AN annotating the anatomical name of the respective anatomical structure. Upon actuating said button Ba, Bb, Bc, the respective angio can be retrieved for display on screen M.

According to one embodiment, graphical user interface controller UIC is configured to generate for display a selectable slice from the reference image PO in the graphical user interface prior to the above mentioned computations by image processor IP. In this "computation on-demand" embodiment, buttons Ba-c are shown for each of the segmented regions of interest and upon actuation of one of the buttons, the respective segmentation is then fed into image processor IP and the above described computation is then executed by identifier ID and associator AS against this requested anatomical structure only and against the angios A received thus far at the image processor IP. In this embodiment, rather than building up the data structure(s) in the background for all pre-defined regions of interest RIOa-c, the data structures DS is built up on demand and is updated only upon the user requesting a specific angio in the pre-op reference image OP.

The components of image processor IP are shown in FIG. 3 all resident on said image processor. However, this is an exemplary embodiment only. In other embodiments, some the components may run in a distributed architecture and are connected in a suitable communication network. In one embodiment the components are running as software routines on computer console CC. The components may also be arranged as dedicated FPGAs or as hardwired standalone chips. The components may be programmed in a suitable scientific computing platform such as Matlab® or Simulink® and then translated into C++ or C routines maintained in a library and linked when called on by image processor IP or computer console CC.

Figure 4:
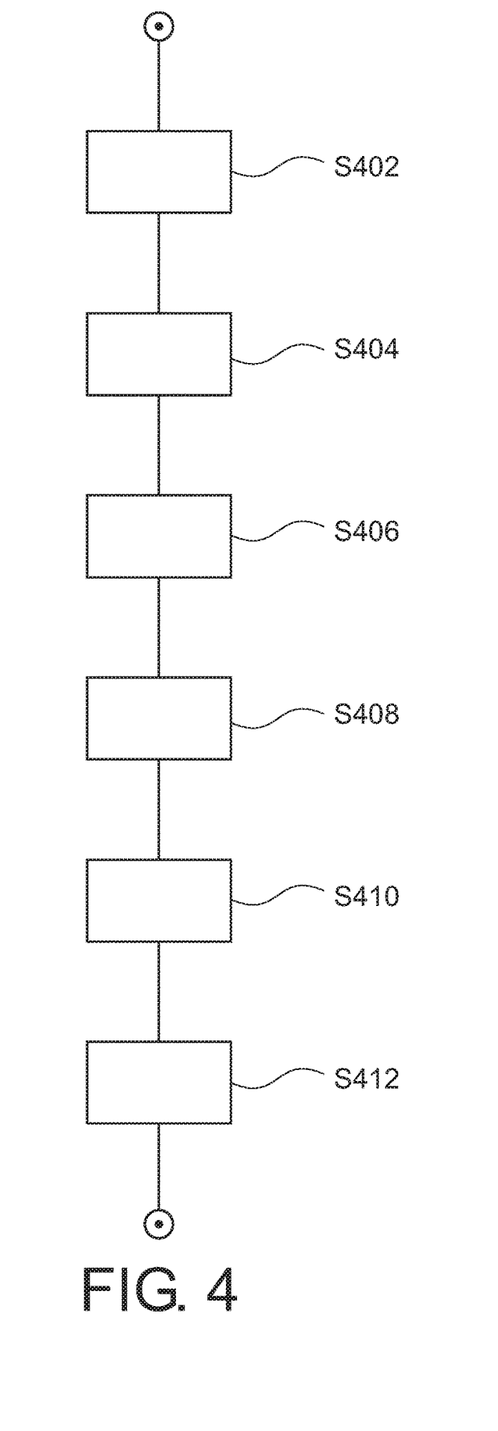
FIG. 4 is a flow chart of an image processing method.

With reference to FIG. 4, steps of an image processing method are shown by means of a flow chart.

At step S402, pre-op CT or MR image PO including annotated image segmentations of the regions of interest ROIa-c are received along with an incoming stream of angios A.

In step S404, the angio frames A1-3 or a selection thereof is registered onto the pre-op reference image PO having the segmentations of the regions of interest ROIa-c. Registration includes registering onto the used X-Ray imager's frame of reference.

In step S406 footprints of the regions of interest ROIa-c in a plurality of the angios are identified that were acquired at a time when the concentration of the previously administered contrast agent at the respective regions of interest ROIa-c was higher than a pre-defined threshold. According to one embodiment this includes identifying for each ROIa-c a main frame where the contrast agent concentration was a maximum at the respective main frame acquisition time but also includes frames acquired within an interval before and after the main frame depending how high the threshold is chosen by the user. The concentration threshold is directly related to pixel grey-values in the images and therefore a corresponding pixel grey-value threshold may be used to determine the main frame.

In one embodiment, the identification step S406 includes detecting for each angio an intermediate anatomic structure perfused when the respective angio was acquired, which structure however was not among the pre-defined regions of interest ROIa-c. The level of perfusion that is how well said structure was filled with contrast agent depends on the threshold setting as used above for identifying the region of interest. Step S406 when operated to include "non-ROI" intermediate anatomic structures is analogous to the detecting of the regions of interest ROIa-c.

In step S408 regions of interest or their segmentations are then associated with respective one of their identified main frames thereby building up an associative ROI-frame data structure. In one embodiment said association is by matching the identified footprints in the angio frames with the segmented ROIs in the pre-op reference image.

In one embodiment, the respective ROIs are also associated with further frames acquired before and after said main frame to so associate with each ROI a collection of frames (including the main frame) that record the passage of the bolus through the respective ROI.

In one embodiment, the non-ROI intermediate anatomic structures are also taken into consideration and the association operation at step S408 includes matching the identified footprints of perfused regions with the non-ROI annotated structures in the registered CT/MR pre-op image.

Step S408 then returns for each angio frame the set of perfused structures which are either ROIs or intermediate structures and/or for each structure or region of interest ROIa-c the best filled frame and according to one embodiment along with the further frames.

At step 410, a graphical user interface is generated and displayed on screen, the GUI including interactive buttons or other selection widgets that allow a user to select any one or more of the regions of interests ROIa-c or possibly intermediate structures. Upon user selection, the respectively associated main frame is then retrieved using the associative data structure and is then displayed on the screen.

In an optional, step 412, either instead or in addition to step S410, the produced associative data structure can be forwarded to other image post-processors.

The above mentioned thresholds used to build the associations are understood to be user definable by setting variables that allow the user to tailor the performance of the system to their needs.

In one embodiment the system may be configured to associate always with the image having the highest maximum contrast for the main frame. However this may not always be appropriate because a quicker response time is required. In some cases the user may be content with the system having found an angio where the respective ROI is sufficiently visible although not necessarily at maximum contrast. The system's response can therefore be adjusted by setting the thresholding in the identifying step S406 as desired. The thresholding used may also take into account the graphics capabilities of the screen M.

Said method can be executed online or offline, that is during acquisition of the angios or after all angios have been acquired.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing apparatus comprising:
an input unit for receiving a stream of frames, the stream of frames acquired whilst a volume of contrast agent is propagating through an object of interest comprising a plurality of regions of interest, the contrast agent volume passing through the plurality of regions of interest sequentially, perfusing respective ones of the plurality of regions of interest as the contrast agent volume propagates through the object;
a registration unit configured to register a plurality of said frames onto a pre-op reference image data set, the reference image data set including a segmentation corresponding to at least one of the regions of interest;
an identifier configured to identify for the at least one of the regions of interest a main frame acquired at a time when a concentration of the contrast agent volume perfusing the at least one region of interest is highest in the at least one region of interest;
an associator configured to associate the at least one of the regions of interest with the identified main frame thereby forming an associative data structure; and
an output unit configured to generate a user interface based on said associative data structure, the user interface, when displayed on a screen, allowing a user to select display of at least one of the plurality of regions of interest, wherein the output unit, in response to said selection, controls the screen to display the main frame associated with the segmentation of the at least one selected region of interest, the user interface thereby enabling temporal navigation through the stream of frames.

2. The image processing apparatus of claim 1, the identifier configured to further identify at least one further frame acquired before or after said respective main frame, the associator configured to associate said further frame with the at least one region of interest segmentation, the associative data structure thereby recording for each region of interest a timeline of the contrast agent perfusion.

3. The image processing apparatus of claim 2, the associator configured to associate to the at least one region of interest a localized curve showing evolution of the contrast agent concentration volume at the at least one region of interest, the curve based on image information in the main frame and further frame.

4. The image processing apparatus of claim 2, wherein the user interface allows the user to toggle through the main and the at least one further frame associated with the at least one region of interest or, if the associative data structure comprises a further one from among the regions of interest, the user interface allows the user to toggle through the main frames and the further frames associated with any one of a user-definable selection from among the at least one region of interest and the further region of interest.

5. The image processing apparatus of claim 1, wherein the identifier is arranged for identifying, as the main frame, a frame acquired at a time when a concentration of the contrast agent volume in the at least one region of interest is at its maximum.

6. The image processing apparatus of claim 1, the generated user interface including at least one interactive button associated with the at least one region of interest, the button bearing an annotation indicative of an anatomical name or function of the at least one region of interest, the button allowing the user to effect the selection of the at least one region of interest.

7. The image processing apparatus of claim 1, wherein the stream of frames comprises a sequence of angiograms acquired by an X-ray imager of the object.

8. The image processing apparatus of claim 1, wherein the reference image data set is a 3D CT or MR image volume of the object.

9. An image processing system comprising: the apparatus of claim 1; an x-ray imager supplying the stream of frames; and a screen.

10. A method of image processing, comprising:
receiving a stream of frames, the stream of frames acquired whilst a volume of contrast agent is propagating through an object of interest comprising a plurality of regions of interest, the contrast agent volume passing through the plurality of regions of interest sequentially and perfusing respective ones of the plurality of regions of interest as the contrast agent volume propagates through the object;
registering a plurality of said frames onto a pre-op reference image data set, the reference image data set including a segmentation corresponding to at least one region of interest of the plurality of regions of interest;
identifying for the at least one region of interest a main frame acquired at a time when a concentration of the contrast agent volume perfusing the at least one region of interest is highest in the at least one region of interest;
associating the at least one region of interest with the identified main frame thereby forming an associative data structure; and
generating a user interface based on said associative data structure, the user interface, when displayed on a screen, allowing a user to select display of the at least one region of interest, an output unit in response to said selection controlling the screen to display the main frame associated with said selected region of interest, the user interface thereby enabling temporal navigation through the stream of frames.

11. The method of claim 10, wherein the step of identifying includes further identifying a further frame acquired before or after said main frame, and the step of associating further includes associating said further frame with the at least one region of interest, the data structure thereby recording for the at least one region of interest a timeline of the contrast agent perfusion.

12. A non-transitory computer readable medium storing instructions, executable by a computer processor, for processing an image, the computer readable medium comprising:
receiving code for receiving a stream of frames, the stream of frames acquired while a volume of contrast agent is propagating through an object of interest comprising a plurality of regions of interest, the contrast agent volume passing through the plurality of regions of interest sequentially and perfusing respective ones of the plurality of regions of interest as the contrast agent volume propagates through the object;
registering code for registering a plurality of the frames of the stream of frame onto a pre-op reference image data set, the reference image data set including a segmentation corresponding to at least one of the plurality of regions of interest;
identifying code for identifying a main frame for the at least one region of interest, the main frame being acquired at a time when a concentration of the contrast agent volume perfusing the at least one region of interest is highest in the at least one region of interest;
associating code for associating the at least one region of interest with the identified main frame thereby forming an associative data structure; and
generating code for generating a graphical user interface based on said associative data structure, the graphical user interface allowing a user to select display of the at least one region of interest, the output unit in response to said selection controlling the screen to display the main frame associated with said selected region of interest, the graphical user interface thereby enabling temporal navigation through the stream of frames.

* * * * *